United States Patent [19]

Conway

[11] 3,958,940

[45] May 25, 1976

[54] METHOD FOR THE REMOVAL OF PENETRANT

[75] Inventor: Edward F. Conway, Arlington Heights, Ill.

[73] Assignee: Magnaflux Corporation, Chicago, Ill.

[22] Filed: Sept. 22, 1975

[21] Appl. No.: 615,406

[52] U.S. Cl. .................. 23/230 L; G01N/33/18
[51] Int. Cl.² .................................... G01N 31/02
[58] Field of Search ................. 23/230 L, 230 R

[56] References Cited
UNITED STATES PATENTS
2,959,471  11/1960  Morgia ........................ 23/230 R OTHER PUBLICATIONS
Morgan et al., Anal. Chem. 14, 725 (1942).
Spring et al., Anal Chem. 18, 201, (1946).
Fink et al., Anal. Chem. 21, 1101, (1949).

*Primary Examiner*—Robert M. Reese
*Attorney, Agent, or Firm*—Hill, Gross, Simpson, Van Santen, Steadman, Chiara & Simpson

[57] ABSTRACT

An improvement in the method of inspecting a test piece for surface flaws in which an oily based dyed penetrant is applied to the test piece and subsequently the test piece is treated with an emulsifying agent to remove excess penetrant from its surface. The improvement is concerned primarily with using an aqueous soap solution as the emulsifying agent, the soap being a water soluble compound of a fatty acid containing from 12 to 20 carbon atoms. The emulsified penetrant is removed by rinsing with an aqueous solution, the emulsified penetrant, residual soap and rinse water are collected and then the collected liquid is reacted with an aqueous solution of a water soluble calcium or magnesium salt to thereby form a readily filterable curd containing the oily penetrant and a substantially dye-free supernatant liquid layer which can be totally separated from each other.

9 Claims, No Drawings

METHOD FOR THE REMOVAL OF PENETRANT

BACKGROUND OF THE INVENTION

1. Field of the Invention

This invention is in the field of removing excess oily based penetrant from the surface of a test piece to which the penetrant has been applied by means of a remover which includes a soap and then precipitating the soap and entrapped penetrant so that a clear supernatant liquid can be recovered either for purposes of recycle or for disposal.

2. Description of the Prior Art

The penetrant method of detecting surface discontinuities in a workpiece is well known. It involves applying a colored oily penetrant to the surface of the test piece and allowing sufficient dwell time for the penetrant to penetrate into any surface flaws. The penetrant may include a visible dye or a fluorescent dye. The excess penetrant is removed from the surface without substantial removal of the penetrant which has become entrapped in any flaws. Then, a developer is added either as a dry developer or as an aqueous or non-aqueous wet developer with or without intermediate drying of the surface. Finally, the surface is inspected for developed cover indications using ordinary light for visibly dyed penetrants, and "black" light if fluorescent penetrant is used.

There have also been numerous disclosures in the prior art of suitable liquid compositions for removing residual films of oil based color penetrants. One such disclosure appears in Mlot-Fijalkowski U.S. Pat. No. 3,558,882 assigned to the assignee of the present application. This patent describes a composition suitable for use as a remover and containing a liquid, water soluble, non-ionic surfactant, a water-immiscible aromatic hydrocarbon solvent having a KB value of at least 70 and a normally liquid, water miscible glycol-ether type of coupler.

While many types of prior art compositions can be used to effectively remove residual films of dyed penetrant from the surface of a test piece, there still remains the problem of disposing of the emulsified penetrant after its removal. This problem is particularly acute in the case of fluorescent penetrants since even a small amount of fluorescent dye in the rinse water is objectionable from the standpoint of reusing the rinse water or disposing of it into sewers.

SUMMARY OF THE INVENTION

The present invention is concerned with both providing an efficient removal for oily based penetrants and is also concerned with rendering the removed penetrant innocuous and in a form in which it can be readily separated from a clear supernatant liquid.

In the process of the present invention, after the oily base dyed penetrant is applied to the test piece and allowed to dwell thereon for a predetermined time, the excess penetrant is removed by treating the surface of the test piece with an aqueous soap solution which operates as an emulsifying agent. The soap is a water soluble compound of a fatty acid containing from 12 to 20 carbon atoms. The emulsified penetrant is then removed and collected along with the rinse water. The collected liquid is then treated with an aqueous solution of a water soluble calcium or magnesium salt, preferably calcium acetate to form a readily filterable curd in which the oily based dyed penetrant is entrapped. This curd containing penetrant tends to sink so that clean water can be removed by allowing the precipitate to settle in a settling tank. Alternatively, the entire bath can be filtered to remove the soap curds and the penetrant, leaving a clear rinse liquid which can be reused as such or discarded without difficulty into a sewer.

DESCRIPTION OF THE PREFERRED EMBODIMENTS

The removers of the present invention can be used in several different ways. For one, they can be used in the form of a bath into which the test piece with the excess penetrant on it is dipped. In such uses, the concentration of the soap emulsifying agent can range from about 5% up to saturation. Since the presence of calcium and/or magnesium ions in tap water may be relatively high and would interfere with the proper emulsification of the penetrant, it is desirable that the solution and the rinse water be made up with deionized water. Alternatively, or in addition to using deionized water, the soap solution can be stabilized against such calcium and magnesium ions through the addition of sequestering agents such as ethylene diamine tetraacetic acid.

Another method for using the removers of the present invention consists in spraying a dilute solution containing 1% or less of the soap onto the test surface, and collecting the rinsings.

Various types of soaps can be used in the remover of the present composition. The most convenient and least expensive soaps are commercial soap flakes which are sodium salts of fatty acids containing from 12 to 20 carbon atoms. When using such soaps, however, it is advisable to incorporate an anti-gelling agent such as butyl carbitol to permit a concentrate to be built up without forming a gel on standing. Typical formulations which can be used in accordance with the present invention are given in the following:

| | Broad range | Preferred |
|---|---|---|
| Soap flakes (88% active) | 8–12% by weight | 10.5% by weight |
| Butyl carbitol | 11.5–14.5% by weight | 13.0% by weight |
| Deionized water | 60–80% by weight | 76.5% by weight |
| Sequestering agents Corrosion inhibitors Coloring dyes | optional, as required | |

In addition to sodium soaps, it is also possible to use amine soaps produced by the condensation reaction between amines such as triethanol amine or mixed isopropanol amines with fatty acids or mixtures of fatty acids particularly those containing between 12 and 20 carbon atoms per molecule. The acid and amine should be in approximately equimolar proportions although an excess of amine is not harmful. Whether used as a dip concentrate or as a spray, this type of soap should be used at a relatively high concentration in water, typically containing at least 25 or 30% soap.

It is most convenient to prepare the remover solution as a concentrate by using the proportions given above, and then dilute the concentrate with 10 parts of water to 1 part of concentrate. These higher dilutions may tend to gel on standing, but if the concentrate is injected into the rinse water just before the rinse water is sprayed onto the test piece, there is no time for gelation to occur, and removal is adequate. The concentrate can be used in dilutions as high as 1 to 50, but with decreased effectiveness.

After the test piece has been treated with the soap solution either by dipping or spraying, it is desirable to remove any residual films by means of a rinse with tap water. The emulsified penetrant, residual soap and rinse water can then be collected and treated by precipitating agents which react with the soap to form water insoluble soaps. Water soluble calcium or magnesium salts are particularly suited for this purpose. For some types of inspection procedures, the chlorides of calcium or magnesium can be used but for the inspection of materials such as aerospace and nuclear components chlorides would not ordinarily be used. The nitrates can be employed in testing inert test pieces but would not be employed where corrosive metals are involved. In general, the acetates of calcium and magnesium are most suitable for use as precipitating agents.

Calcium or magnesium acetates should be added to the collected rinsings in water solution. If added as a powder, they sometimes form a thick and hard to dissolve paste with the soap. The acetates should be added in approximately stoichiometric amounts, based on the concentration of soap. From about ⅔ to 1½ or more equivalents of the acetate are normally to be used for one equivalent weight of soap.

The precipitate which results is a readily filterable curd containing the oily based dyed penetrant substantially immobilized therein. The precipitate tends to sink, so that it can be settled out in a settling tank and the clean supernatant water removed. Alternatively, the whole bath can be filtered to remove the soap curds and penetrants, leaving a relatively clean rinse water.

Two percent soap solutions of different soaps were sprayed onto an aluminum block and a sandblasted panel after these test pieces had been treated with a commercial fluorescent penetrant for 10 minutes. The soap solution was made by dissolving 2 grams of soap flakes (Amber flakes) supplied by Procter and Gamble in hot water. The sprayed soap solution removed most of the penetrant in the case of the aluminum block, leaving only a slight background. A complete wash with the sprayed soap solution was effected in the case of the sandblasted panel.

Another 2% solution of soap flakes ("Ivory" chips supplied by Procter and Gamble) was made up. Removal of residual penetrant was also effected for both the block and panel, with only slight background fluorescence remaining.

After rinsing of the soap from the blocks and the panels with water, the addition of 10% or 1% solutions of calcium acetate to the rinsings produced two distinct layers which were separable by gravity filtration. Fluffy yellow solids remained in the filtering funnel and clear water, free of fluorescence was obtained.

From the foregoing, it will be seen that the process of the present invention provides an efficient means of removing oily base penetrants from the surfaces of test pieces and rendering such penetrants innocuous. It should also be understood that various modifications could be made to the described embodiments without departing from the scope of the present invention.

I claim as my invention:

1. In the method of inspecting a test piece for surface flaws in which an oily based dyed penetrant is applied to the test piece and subsequently said test piece is treated with an emulsifying agent to remove excess penetrant from its surface, the improvement whereby said excess penetrant is rendered innocuous, said improvement comprising employing an aqueous soap solution as said emulsifying agent, the soap being a water soluble compound of a fatty acid containing from 12 to 20 carbon atoms, removing the emulsified penetrant by rinsing with an aqueous solution, collecting the emulsified penetrant, residual soap and rinse water, and treating the collected liquid with an aqueous solution of a water soluble calcium or magnesium salt to thereby form a readily filterable curd containing said oily based dyed penetrant and a substantially dye-free liquid layer.

2. The method of claim 1 in which said soap is a sodium salt of said fatty acid.

3. The method of claim 1 in which said soap is an amine salt of said fatty acid.

4. The method of claim 1 in which said aqueous soap solution includes a sequestering agent.

5. The method of claim 1 in which said water soluble salt is calcium acetate.

6. The method of claim 1 in which said test piece is immersed in a bath of said emulsifying agent.

7. The method of claim 1 in which said emulsifying agent is sprayed onto the surface of said test piece.

8. The method of claim 1 in which said aqueous soap solution contains butyl carbitol as a gel preventing agent.

9. The method of claim 8 in which said calcium acetate is added in an amount of from ⅔ to 1½ equivalents per equivalent weight of soap.

* * * * *